United States Patent
Sela et al.

(10) Patent No.: US 10,828,107 B2
(45) Date of Patent: Nov. 10, 2020

(54) MIXED REALITY TRAINING SYSTEM

(71) Applicants: SYNAPTIVE MEDICAL (BARBADOS) INC., Bridgetown (BB); Gal Sela, Toronto (CA); Fergal Kerins, Toronto (CA); Kamyar Abhari, Toronto (CA); Kirusha Srimohanarajah, Toronto (CA)

(72) Inventors: Gal Sela, Toronto (CA); Fergal Kerins, Toronto (CA); Kamyar Abhari, Toronto (CA); Kirusha Srimohanarajah, Toronto (CA)

( * ) Notice: Subject to any disclaimer, the term of this patent is extended or adjusted under 35 U.S.C. 154(b) by 405 days.

(21) Appl. No.: 15/571,554

(22) PCT Filed: Oct. 21, 2016

(86) PCT No.: PCT/CA2016/000266
§ 371 (c)(1),
(2) Date: Nov. 3, 2017

(87) PCT Pub. No.: WO2018/071999
PCT Pub. Date: Apr. 26, 2018

(65) Prior Publication Data
US 2019/0380780 A1  Dec. 19, 2019

(51) Int. Cl.
*A61B 34/10* (2016.01)
*G09B 23/28* (2006.01)
*A61B 34/20* (2016.01)

(52) U.S. Cl.
CPC .............. *A61B 34/10* (2016.02); *A61B 34/20* (2016.02); *G09B 23/28* (2013.01);
(Continued)

(58) Field of Classification Search
CPC ....... G09B 23/28; G09B 23/285; G09B 23/34
See application file for complete search history.

(56) References Cited

U.S. PATENT DOCUMENTS

| 8,311,791 B1 | 11/2012 | Avisar |
| 8,831,924 B2 | 9/2014 | Avisar |

(Continued)

FOREIGN PATENT DOCUMENTS

| WO | 2014052158 A2 | 4/2014 | |
| WO | WO-2014139024 A1 * | 9/2014 | ........... A61B 5/0042 |
| WO | 2014052158 A3 | 7/2015 | |

OTHER PUBLICATIONS

PCT International Search Report, dated Jun. 16, 2014, PCT/CA2016/000266.

(Continued)

*Primary Examiner* — Eddy Saint-Vil (57) ABSTRACT

A training system for training a trainee to perform a surgical procedure on an anatomical region. The system includes a physical model of the anatomical region, a physical training instrument, a tracking system configured to track the location and orientation of the physical training instrument relative to the physical model, a display device, and a computer system. The computer system receives from the tracking system information indicating the location and orientation of the physical training instrument and generates and displays an augmented physical model and the physical training instrument. The display is updated based as the trainee manipulates the physical training instrument. After the trainee has completed the surgical procedure, the computer calculates a score based on the performance of the trainee. The score is a measure of the accuracy of the surgical procedure performed by the trainee or the duration of the surgical procedure.

20 Claims, 8 Drawing Sheets

(52) U.S. Cl.
CPC ... *A61B 2034/104* (2016.02); *A61B 2034/107* (2016.02); *A61B 2034/108* (2016.02); *A61B 2034/2055* (2016.02); *A61B 2034/2065* (2016.02)

(56) References Cited

U.S. PATENT DOCUMENTS

| | | | |
|---|---|---|---|
| 9,129,054 B2 | 9/2015 | Nawana et al. | |
| 9,251,721 B2 | 2/2016 | Lampotang et al. | |
| 2007/0021738 A1* | 1/2007 | Hasser | A61B 90/37 606/1 |
| 2009/0263775 A1 | 10/2009 | Ullrich | |
| 2010/0167249 A1 | 7/2010 | Ryan | |
| 2010/0178644 A1 | 7/2010 | Meglan et al. | |
| 2012/0045742 A1* | 2/2012 | Meglan | G09B 23/28 434/268 |
| 2012/0225413 A1* | 9/2012 | Kotranza | G09B 23/30 434/262 |
| 2013/0047103 A1 | 2/2013 | Avisar | |
| 2013/0323700 A1 | 12/2013 | Samosky et al. | |
| 2015/0037775 A1* | 2/2015 | Ottensmeyer | G09B 23/34 434/271 |
| 2015/0140535 A1 | 5/2015 | Geri et al. | |
| 2015/0381345 A1* | 12/2015 | Thomas | H04J 3/0602 370/509 |
| 2016/0070436 A1* | 3/2016 | Thomas | A61B 5/055 715/771 |
| 2016/0225192 A1* | 8/2016 | Jones | G06F 3/012 |
| 2018/0140362 A1* | 5/2018 | Cal | A61B 34/25 |

OTHER PUBLICATIONS

Botden et al, "What is going on in augmented reality simulation in laparoscopic surgery?", Surg Endosc (2009) 23:1693-1700.
"Haptica and Royal College of Surgeons in Ireland to introduce new approaches to surgical education", http://www.hoise.com/vmw/06/articles/vmw/LVVM120618.html, visited on Dec. 24, 2015.
CAE ProMIS Laproscopic Simulator Brochure, 2012 CAE Healthcare 345-0712.
Sielhorst et al, "An Augmented Reality Delivery Simulator for Medical Training", AMI-ARCS'04.

* cited by examiner

MIXED REALITY TRAINING SYSTEM

TECHNICAL FIELD

The subject matter of the present disclosure generally relates to the field of systems for training and evaluating the performance surgeons. More particularly, the subject matter of the present disclosure technically relates to mixed reality systems for training and evaluating the performance of surgeons employing a physical phantom that is augmented with virtual elements.

BACKGROUND

In the field of medicine, various computerized systems have been developed to assist in the training of surgeons employing virtual reality and augmented reality approaches. Such approaches allow trainee surgeons to perform simulated surgical procedures either on virtual elements representing a portion of a patient's body or in some cases on a combination of a physical model and virtual elements. While such systems may provide useful experience to the trainee, they fail to provide feedback on the performance of the trainee. An expert surgeon can observe all or part of such a simulated operation, either in real-time or by viewing a recording, and then assess the trainee's performance, but such an approach is generally undesirable. Such an approach is subjective and the results will vary depending on the expert doing the evaluation, and it is costly in terms of the requirement for an expert's time.

SUMMARY

The invention described herein provides a surgical training system for training a trainee to perform a surgical procedure on an anatomical region of a body, such as a human body. The system includes a physical model of the anatomical region, a physical training instrument, a tracking system configured to track the location and orientation of the physical training instrument relative to the physical model, a display device viewable by the trainee, and a computer system electronically connected to the tracking system and the display device. The computer system is configured to receive from the tracking system information indicating the location and orientation of the physical training instrument. The computer system generates and displays on the display device a display showing an augmented physical model and the physical training instrument. The display is updated based on changes in the location and orientation of the physical training instrument relative to the physical model as the trainee manipulates the physical training instrument to perform the surgical procedure. After the trainee has completed the surgical procedure, the computer system calculates a score based on the performance of the trainee and stores the score in a computer readable memory. The score is based on a measure of the accuracy of the surgical procedure performed by the trainee.

The tracking system may include a video camera that provides a real-time stream of video showing a portion of the physical model upon which the surgical procedure is being performed, and the computer system generates and updates the augmented physical model based on the video.

The generated display may include virtual elements rendered by the computer system and superimposed on a digital rendering of the physical model. The virtual elements may include highlighting of a portion of the digital rendering of the physical model.

The score is preferably further based on the duration of the surgical procedure.

The anatomical region may be a portion of a mammalian head and the virtual elements may include neural tracts in a brain. In such embodiments, the score may be based on a tract impact score that provides a measure of the impact of the surgical procedure on the neural tracts.

The anatomical region may be a portion of a mammalian brain having a tumor, and the augmented physical model may include a simulated tumor. In such embodiments, the surgical procedure may involve performing a craniotomy and resectioning of the tumor. The score may be based on a measure of the damage to healthy brain tissue caused by the surgical procedure. The score may be alternatively or additionally calculated based on the distance from the craniotomy to the tumor. The score may be calculated based on the amount of non-tumor tissue in the brain that would have been removed or damaged by a surgical instrument corresponding to the physical training instrument by movements of the surgical instrument corresponding to trainee's manipulation of the physical training instrument. The score may be calculated based on an estimate of the impact of the surgical procedure on neural tracts in the brain. The score may be calculated based on the amount of the tumor that would have been removed by a surgical instrument corresponding to the physical training instrument by movements of the surgical instrument corresponding to trainee's manipulation of the physical training instrument. The computer system may further generate and display as part of the augmented physical model an artery proximate to the tumor.

The method of calculating the score may be derived from analysis of the performance of an expert performing the surgical procedure. The method of calculating the score may be more preferably derived from analysis of the performance of a plurality of experts performing the surgical procedure using machine learning.

The display device may be a head-mounted display worn by the trainee. The tracking system may be further configured to track the location of the trainee's head relative to the physical model so that the display is generated from the perspective of the trainee based on the location of the trainee's head. Then the display is updated as the location of the trainee's head changes. The system may further include a head-mounted display worn by a trainer, and the tracking system may be further configured to track the location of the trainer's head relative to the physical model. Then the computer system is further configured to generate and display on the head-mounted display worn by the trainer a display comprising the augmented physical model and the physical training instrument from the perspective of the trainer. In such embodiments, the display on the head-mounted display worn by the trainer is updated based on changes in the location and orientation of the physical training instrument relative to the physical model as the trainee manipulates the physical training instrument to perform the surgical procedure, and the display on the head-mounted display worn by the trainer is updated as the location of the trainer's head changes.

The computer system may be further configured to generate and display on the display device an augmented physical training instrument. The location and orientation of the augmented physical training instrument relative to the augmented physical model as depicted in the image may be based on the location and orientation of the physical training instrument relative to the physical model. The displayed augmented physical training instrument may be updated on the display device by the computer system as the trainee manipulates the physical training instrument.

The physical training instrument may resemble a portion of a surgical instrument, and the augmented physical training instrument may be a digital rendering of the physical training instrument augmented by a tip portion generated by the computer system so that the augmented physical training instrument appears on the display device to be the surgical instrument. Then, as the trainee manipulates the physical training instrument, the computer system may repeatedly generate and display on the display device the augmented physical model depicting simulated effects of the surgical instrument on the anatomical region. The system may further include a haptic feedback mechanism coupled to the physical training instrument and configured to provide haptic feedback to the trainee under control of the computer system by applying force to the physical training instrument as the trainee moves the physical training instrument.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In one non-limiting example, the terms "about", "approximately", and "substantially" mean plus or minus 10 percent or less.

As used herein the phrase "surgical tool" or "surgical instrument" refers to any item that may be directed to a site along a path in the patient's body. Examples of surgical tools include (but are not necessarily limited to) scalpels, resecting devices, imaging probes, sampling probes, catheters, and any other device that may access a target location within the patient's body (or aid another surgical tool in accessing a location within a patient's body), whether diagnostic or therapeutic in nature.

Unless defined otherwise, all technical and scientific terms used herein are intended to have the same meaning as commonly understood by one of ordinary skill in the art. Unless otherwise indicated, such as through context, as used herein, the following terms are intended to have the following meanings:

As used herein, the phrase "access port" refers to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

The present disclosure is generally related to medical procedures, neurosurgery, and minimally invasive surgery.

In the example of a port-based surgery, a surgeon or robotic surgical system may perform a surgical procedure involving tumor resection in which the residual tumor remaining after is minimized, while also minimizing the trauma to the healthy white and grey matter of the brain.

Figure 1:
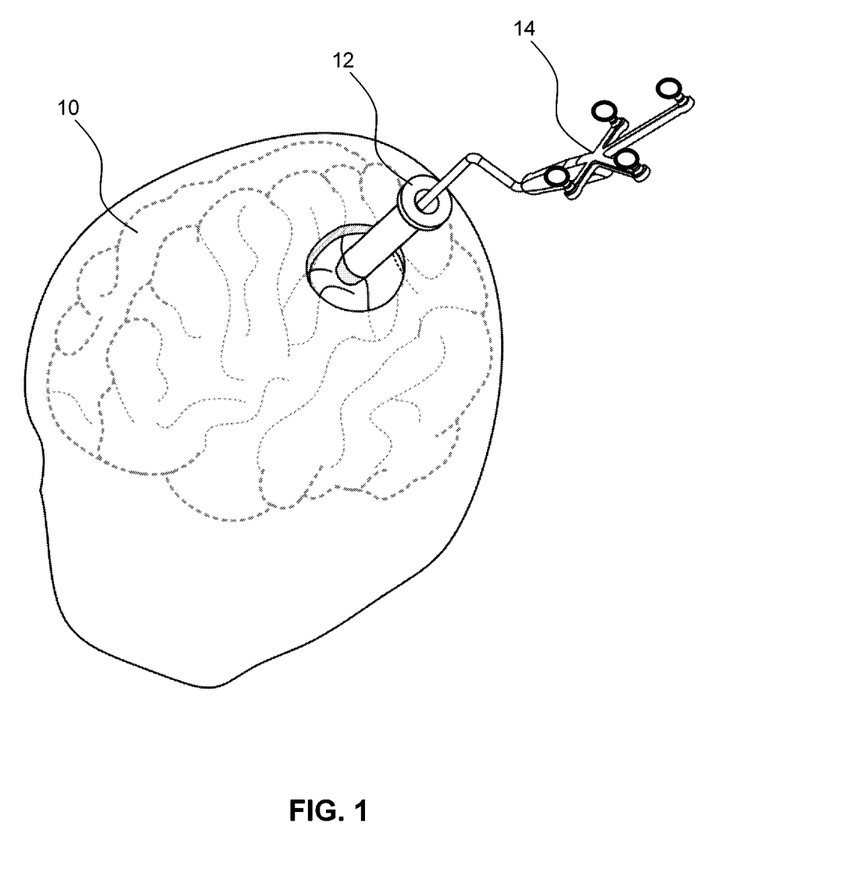
FIG. 1 illustrates the insertion of an access conduit into a human brain, for providing access to internal brain tissue during a medical procedure.

FIG. 1 illustrates the insertion of an access port into a human brain, for providing access to internal brain tissue during a medical procedure. In FIG. 1, access port 12 is inserted into a human brain 10, providing access to internal brain tissue. Access port 12 may include instruments such as catheters, surgical probes, or cylindrical ports such as the NICO BrainPath™. Surgical tools and instruments may then be inserted within the lumen of the access port in order to perform surgical, diagnostic or therapeutic procedures, such as resecting tumors as necessary. The present disclosure applies equally well to catheters, DBS needles, a biopsy procedure, and also to biopsies and/or catheters in other medical procedures performed on other parts of the body where head immobilization is needed.

In the example of a port-based surgery, a straight or linear access port 12 is typically guided down a sulci path of the brain. Surgical instruments 14 may then be inserted down the access port 12.

Optical tracking systems, which may be used in the medical procedure, track the position of a part of the instrument that is within line-of-site of the optical tracking camera. These optical tracking systems also require a reference to the patient to know where the instrument is relative to the target (e.g., a tumor) of the medical procedure. These optical tracking systems require a knowledge of the dimensions of the instrument being tracked so that, for example, the optical tracking system knows the position in space of a tip of a medical instrument relative to the tracking markers being tracked. It should be noted that any embodiments provided herein using which employ an optical tracking system may be extended to any relevant tracking system as are known in the art, and thus the examples provided below should not be taken to limit the scope of the invention as disclosed herein.

Figure 2:
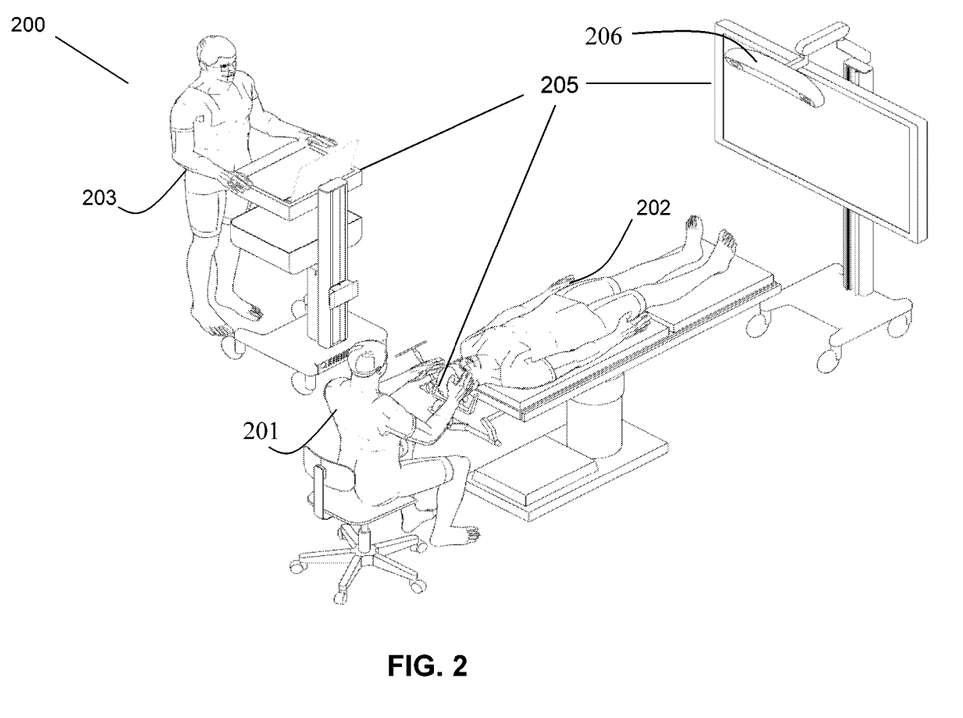
FIG. 2 shows an exemplary navigation system to support minimally invasive access port-based surgery.

Referring to FIG. 2, an exemplary navigation system environment 200 is shown, which may be used to support navigated image-guided surgery. As shown in FIG. 2, surgeon 201 conducts a surgery on a patient 202 in an operating room (OR) environment. A medical navigation system 205 comprising an equipment tower, tracking system 206, displays and tracked instruments assist the surgeon 201 during his procedure. An operator 203 is also present to operate, control and provide assistance for the medical navigation system 205. A detailed description of a surgical navigation system is outlined in international application PCT/CA2014/050270, entitled "SYSTEMS AND METHODS FOR NAVIGATION AND SIMULATION OF MINIMALLY INVASIVE THERAPY", which claims priority to U.S. Provisional Patent Application Ser. Nos. 61/800,155 and 61/924,993, which are all hereby incorporated by reference in their entirety.

Figure 3:
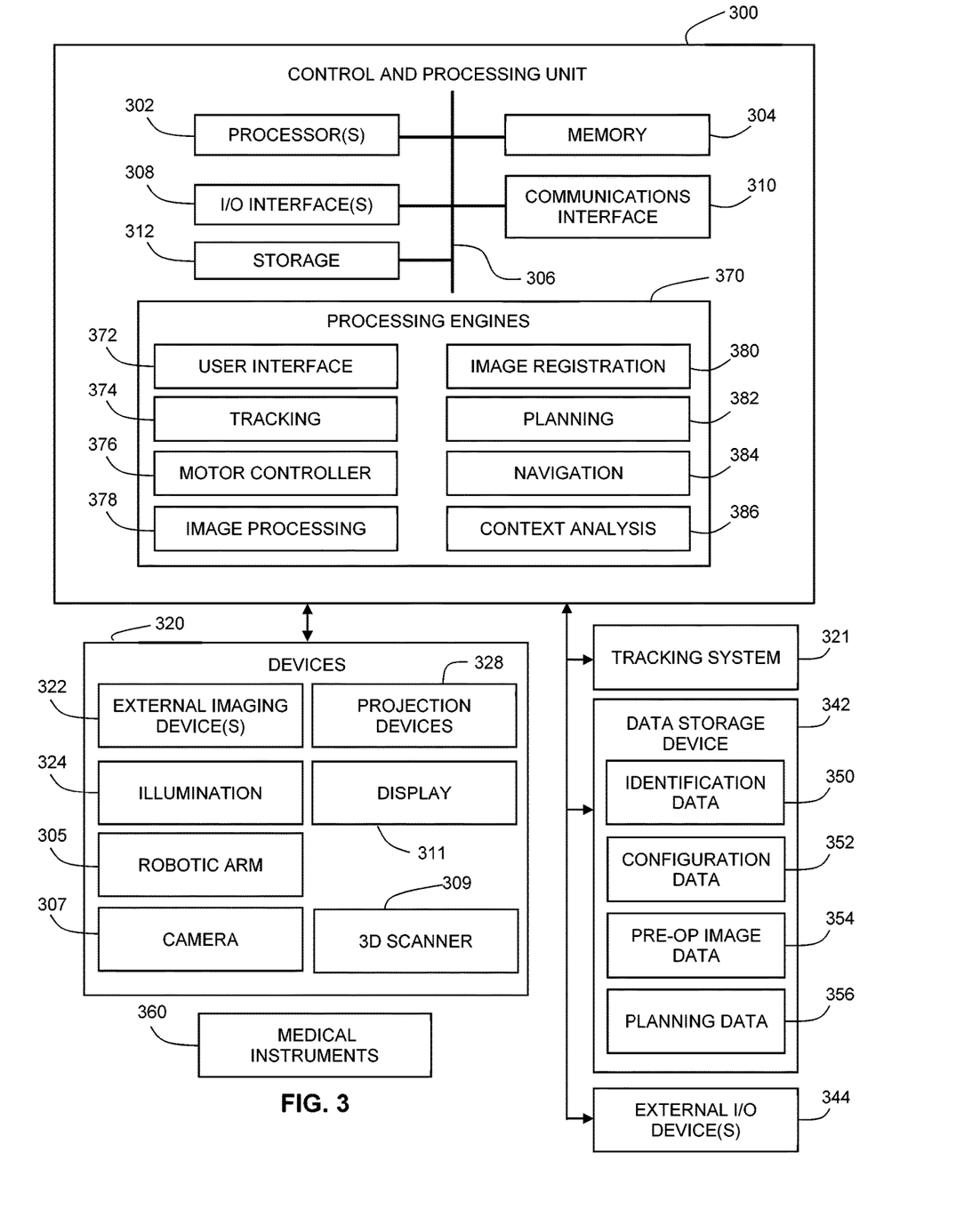
FIG. 3 is a block diagram illustrating a control and processing system that may be used in the navigation system shown in FIG. 2.

Referring to FIG. 3, a block diagram is shown illustrating a control and processing system 300 that may be used in the medical navigation system 200 shown in FIG. 2 (e.g., as part of the equipment tower). As shown in FIG. 3, in one example, control and processing system 300 may include one or more processors 302, a memory 304, a system bus 306, one or more input/output interfaces 308, a communications interface 310, and storage device 312. Control and processing system 300 may be interfaced with other external devices, such as tracking system 321, data storage 342, and external user input and output devices 344, which may include, for example, one or more of a display, keyboard, mouse, sensors attached to medical equipment, foot pedal, and microphone and speaker. Data storage 342 may be any suitable data storage device, such as a local or remote computing device (e.g. a computer, hard drive, digital media device, or server) having a database stored thereon. In the example shown in FIG. 3, data storage device 342 includes identification data 350 for identifying one or more medical instruments 360 and configuration data 352 that associates customized configuration parameters with one or more medical instruments 360. Data storage device 342 may also include preoperative image data 354 and/or medical procedure planning data 356. Although data storage device 342 is shown as a single device in FIG. 3, it will be understood that in other embodiments, data storage device 342 may be provided as multiple storage devices.

Medical instruments 360 are identifiable by control and processing unit 300. Medical instruments 360 may be connected to and controlled by control and processing unit 300, or medical instruments 360 may be operated or otherwise employed independent of control and processing unit 300. Tracking system 321 may be employed to track one or more of medical instruments 360 and spatially register the one or more tracked medical instruments to an intraoperative reference frame. For example, medical instruments 360 may include tracking markers such as tracking spheres that may be recognizable by a tracking camera 307. In one example, the tracking camera 307 may be an infrared (IR) tracking camera. In another example, a sheath placed over a medical instrument 360 may be connected to and controlled by control and processing unit 300.

Control and processing unit 300 may also interface with a number of configurable devices, and may intraoperatively reconfigure one or more of such devices based on configuration parameters obtained from configuration data 352. Examples of devices 320, as shown in FIG. 3, include one or more external imaging devices 322, one or more illumination devices 324, an automated arm 305, one or more projection devices 328, one or more 3D scanning devices 309 (such as 3D scanners or structured light scanners), and one or more displays 311. Examples of external imaging devices 322 include optical coherence tomography (OCT), computed tomography (CT), magnetic resonance imaging (MRI), positron emission tomography (PET) and ultrasound (US) imaging devices.

Exemplary aspects of the disclosure can be implemented via processor(s) 302 and/or memory 304. For example, the functionalities described herein can be partially implemented via hardware logic in processor 302 and partially using the instructions stored in memory 304, as one or more processing modules or engines 370. Example processing modules include, but are not limited to, user interface engine 372, tracking module 374, motor controller 376, image processing engine 378, image registration engine 380, procedure planning engine 382, navigation engine 384, and context analysis module 386. While the example processing modules are shown separately in FIG. 3, in one example the processing modules 370 may be stored in the memory 304 and the processing modules may be collectively referred to as processing modules 370.

It is to be understood that the system is not intended to be limited to the components shown in FIG. 3. One or more components of the control and processing system 300 may be provided as an external component or device. In one example, navigation module 384 may be provided as an external navigation system that is integrated with control and processing system 300.

Some embodiments may be implemented using processor 302 without additional instructions stored in memory 304. Some embodiments may be implemented using the instructions stored in memory 304 for execution by one or more general purpose microprocessors. Thus, the disclosure is not limited to a specific configuration of hardware and/or software.

While some embodiments can be implemented in fully functioning computers and computer systems, various embodiments are capable of being distributed as a computing product in a variety of forms and are capable of being applied regardless of the particular type of machine or computer readable media used to actually effect the distribution.

According to one aspect of the present application, one purpose of the navigation system 205, which may include control and processing unit 300, is to provide tools to the trainee neurosurgeon that will lead to the most informed, least damaging neurosurgical operations. In addition to removal of brain tumors and intracranial hemorrhages (ICH), the navigation system 205 can also be applied to a brain biopsy, a functional/deep-brain stimulation (DBS), a catheter/shunt placement procedure, open craniotomies, endonasal/skull-based/ENT, spine procedures, and other parts of the body such as breast biopsies, liver biopsies, etc. While several examples have been provided, aspects of the present disclosure may be applied to any suitable medical procedure.

While one example of a navigation system 205 is provided that may be used with aspects of the present application, any suitable navigation system may be used, such as a navigation system using magnetic tracking instead of infrared cameras, and or active tracking markers.

The system of according to the present invention employs a physical model or phantom of an anatomical region. For example, the phantom may be brain model that is suitable for simulating the surgical procedure through one or more layers of the head. Such phantoms are described in international application PCT/CA2014/050659, the entire contents of which is incorporated herein by refer. Such a procedure may involve perforating, drilling, boring, punching, piercing, or any other suitable methods, as necessary for an endo-nasal, port-based, or traditional craniotomy approach. For example, some embodiments of the present disclosure provide brain models comprising an artificial skull layer that is suitable for simulating the process of penetrating a mammalian skull. As described in further detail below, once the skull layer is penetrated, the medical procedure to be simulated using the training model may include further steps in the diagnosis and/or treatment of various medical conditions. Such conditions may involve normally occurring structures, aberrant or anomalous structures, and/or anatomical features underlying the skull and possibly embedded within the brain material.

In some example embodiments, the brain model is suitable for simulating a medical procedure involving a brain tumor that has been selected for resection. In such an example embodiment, the brain model is comprised of a brain material having a simulated brain tumor provided therein. This brain material simulates, mimics, or imitates at least a portion of the brain at which the medical procedure is directed or focused.

Referring to FIGS. 4-8, an exploded view of an example model or phantom shown generally at is provided that is suitable for use in training or simulation of a medical procedure which is invasive of a mammalian head, generally being a human head. The training model may be adapted or designed to simulate any mammalian head or a portion thereof. It is to be understood that the person to be trained may be selected from a wide variety of roles, including, but not limited to, a medical doctor, resident, student, researcher, equipment technician, or other practitioner, professionals, or personnel. In other embodiments, the models provided herein may be employed in simulations involving the use of automated equipment, such as robotic surgical and/or diagnostic systems.

Figure 4:
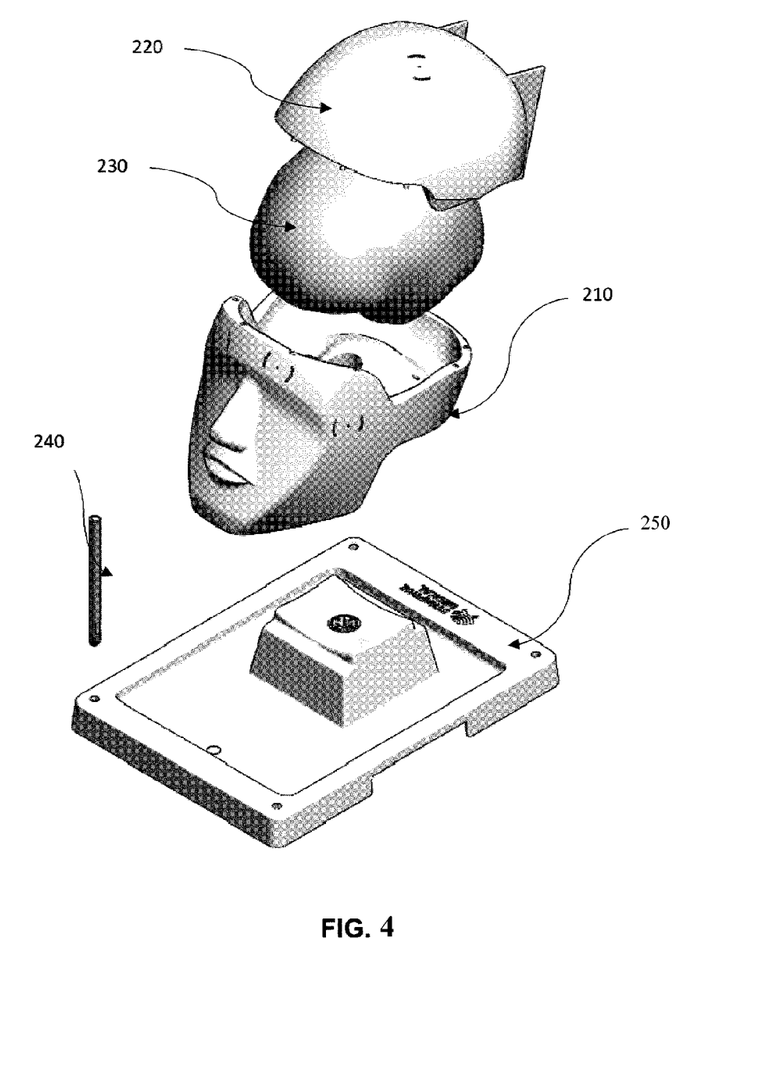
FIG. 4 is an illustration of an example training model in an exploded view, illustrating parts of the base component and the training component.

Referring now to FIG. 4, an exploded view of an example implementation of training model is shown that includes a base component and a training component. The base component is comprised of a tray component (250) and a head component. The head component is comprised of a bowl component (210) and a skull component (220). The training component may be comprised of a brain (230) with the following layers: dura, CSF (cerebrospinal fluid), vessels, white matter, grey matter, fiber bundles or tracks, target tumors, or other anomalous structures. The training component may also include the aforementioned skull component (220) when crafted in a skull mimicking material. Optionally, the training model may be also comprised of a covering skin layer (not shown). Further, the base component may include a holder (240) provided on the tray (250) to facilitate easy mounting of fiducials or reference points for navigation.

Figure 5:
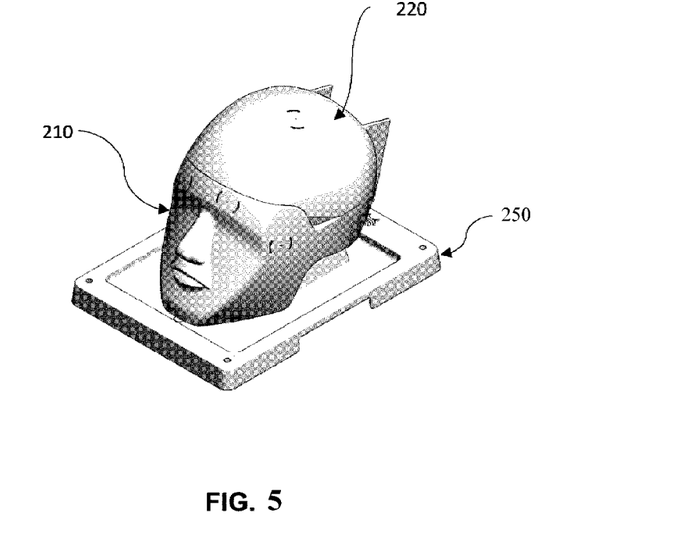
FIG. 5 is an illustration of an example base component of the training model illustrating the tray, the head and the skull.
Figure 6:
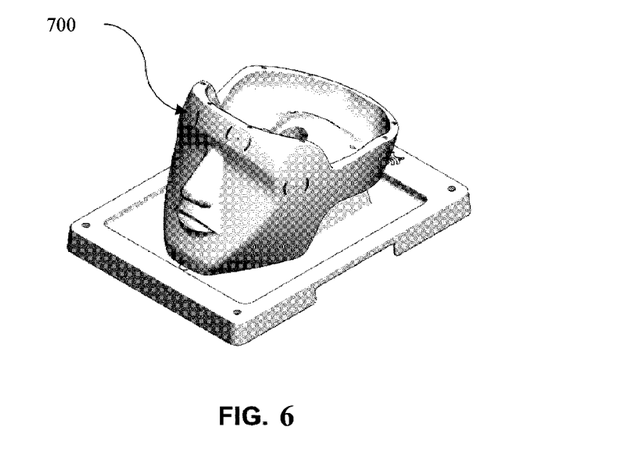
FIG. 6 is an illustration of an example base component of the training model without the skull section, illustrating fiducials that are important for registration of images acquired using different modalities.
Figure 7:
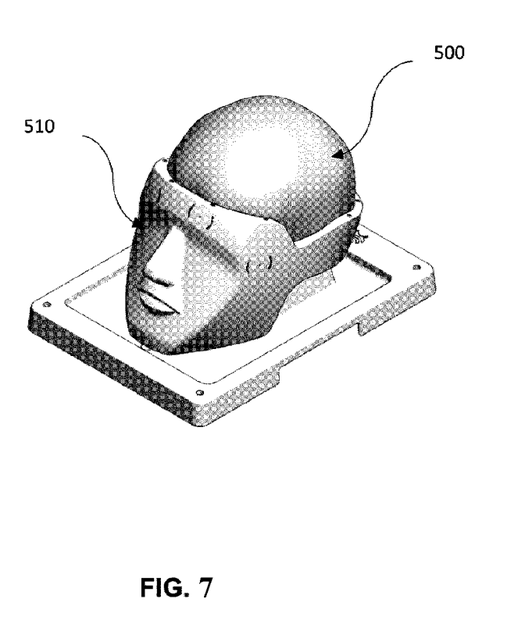
FIG. 7 is an illustration of an example base component of the training model, shown containing the training component.
Figure 8:
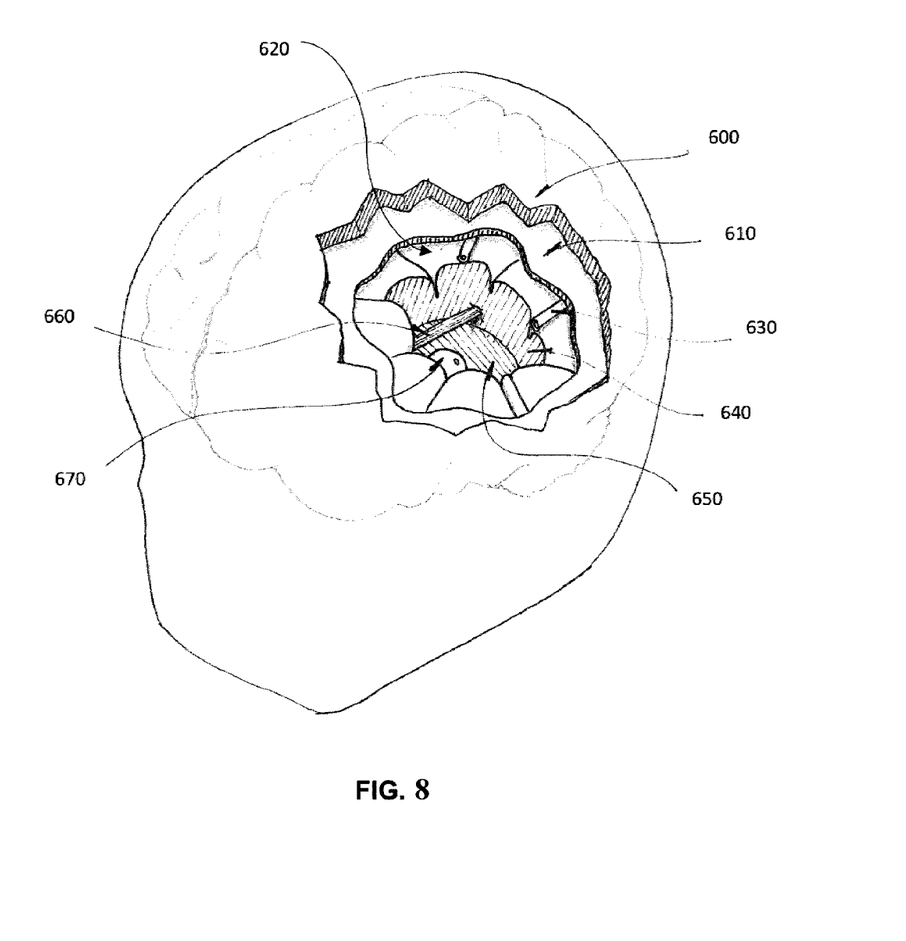
FIG. 8 is an illustration providing a detail view of an example training component, illustrating various clinically relevant example components that may be emulated in the model.

Referring to FIGS. 5-7, the tray component (250) forming part of the base component defines a training receptacle which includes a pedestal section (242) which is sized and configured for receipt of the bowl component (210) therein. Thus the training component is sized, configured or otherwise adapted to be compatible with, or complementary to the base component, and particularly the training component receptacle, such that the base component and the training component may be assembled to provide the assembled training model.

The base component may have any size, shape and configuration capable of maintaining the training component, mounted within the training component receptacle, in a position suitable for performing the medical procedure to be trained. This base component comprises features that enable registration, such as fiducials, touchpoint locations, and facial contours for 3D surface scanning, MR, CT, OCT, US, PET, optical registration or facial registration. Furthermore, the base component is adapted or configured to maintain the training component in a relatively stable or fixed position throughout the performance of the medical procedure to be simulated during the training procedure. The base component provides both mechanical support during the training procedure and aids in the proper orientation of the training components to mimic actual positioning of a patient's head during the surgical procedure.

Referring to FIGS. 4 and 5, the base component may be comprised of a head component (210) and a tray component (250). The tray component (250) is sized, configured or otherwise adapted to be compatible with, or complementary to the head component (210). The tray component (250) is adapted or configured to maintain the head component (210) in a relatively stable or fixed position throughout the performance of the imaging or medical procedure to be simulated. This may be accomplished with the use of a mechanical feature such as a snap mechanism that exists to affix the head component (210) to the tray component (250). The tray component (250) may contain a trough (244) to catch liquids, and insertion points to affix hardware to aid with image registration and/or the medical procedure to be trained.

The head component (210) is sized, configured or otherwise adapted to be compatible with, or complementary to the tray component (250) and the training component. The head component (210) is adapted or configured to maintain the training component (230) (located under skull component 300) in a relatively stable or fixed position throughout the performance of the medical procedure to be simulated. This head component (210) is adapted or configured to enable anatomically correct surgical positioning. This may include affixing the head component (210) with a surgical skull clamp or headrest, for example a Mayfield skull clamp. This head component (210) is also adapted or configured to enable anatomically correct imaging positioning for any contemplated imaging modality including, but not limited to, MR, CT, OCT, US, PET, optical registration or facial registration. For example the head component (210) may be positioned in a supine position within an MRI apparatus to enable anatomically accurate coronal image acquisition.

In some embodiments, the head component (210) is shaped or configured to simulate a complete or full skull. In other words, the training component comprises bowl section (210) and skull section (220), while the bowl section (210) comprises a further portion of a complete skull and head. In some embodiments, as shown in FIG. 2, the head component i.e., bowl section (210) and skull section (220), and training component (230) together provide a complete simulated skull or together provide a simulated head including skull (220) and brain (230). The simulated head provided by the training model enhances the reality of the overall simulation training experience.

In addition, the base and training components of the training model, and particularly the head component, may also include one or more external anatomic landmarks or fiducial locations 700, as shown in FIG. 6, such as those likely to be relied upon by the trainee for image registration for example, touchpoints, the orbital surface, nasal bone, middle nasal concha, inferior nasal concha, occipital bone, nape, and nasal passage. These features will aid in registering the training component with the preoperative images, such as MR, CT, OCT, US, PET, so that the surgical tools can be navigated appropriately.

In this regard, navigation to establish the location of the hole or passage through the skull of the patient during a craniotomy procedure is often critical for the success of the medical procedure. Accordingly, external anatomic landmarks and/or touchpoints are provided by the simulated head in order to provide training on the correct registration of the training model with the acquired images. These anatomic landmarks and touchpoints may be utilized for attaching registration hardware, for example a facial registration mask or fiducial landmark. Thus, the training model, and particularly the simulated head, are sized, configured and shaped to approximate and closely resemble the size, configuration and shape of the head of a patient on which the medical procedure is to be performed. In other words, the head component may be both 'life-like' and 'life-sized'.

The base component may be comprised of any composition or material suitable for providing the training component receptacle, and may be suitable for being cast, molded or otherwise configured to provide or support the simulated head when assembled with the training component. For instance, the base component may be comprised of any suitable casting compound, casting composition or plaster. The base component may be comprised of a material that is rigid, non-reflective, non-ferrous, non-porous, cleanable, and lightweight, for example a urethane or acrylonitrile butadiene styrene (ABS). In addition, the bowl (210) and skull (220) components of the base component may be comprised of a material that is visible by the imaging procedure of interest to enable registration. The material for the bowl (210) and skull (220) components of the base may therefore be selected to be visible by MR, CT, and/or PET.

Figure 9:
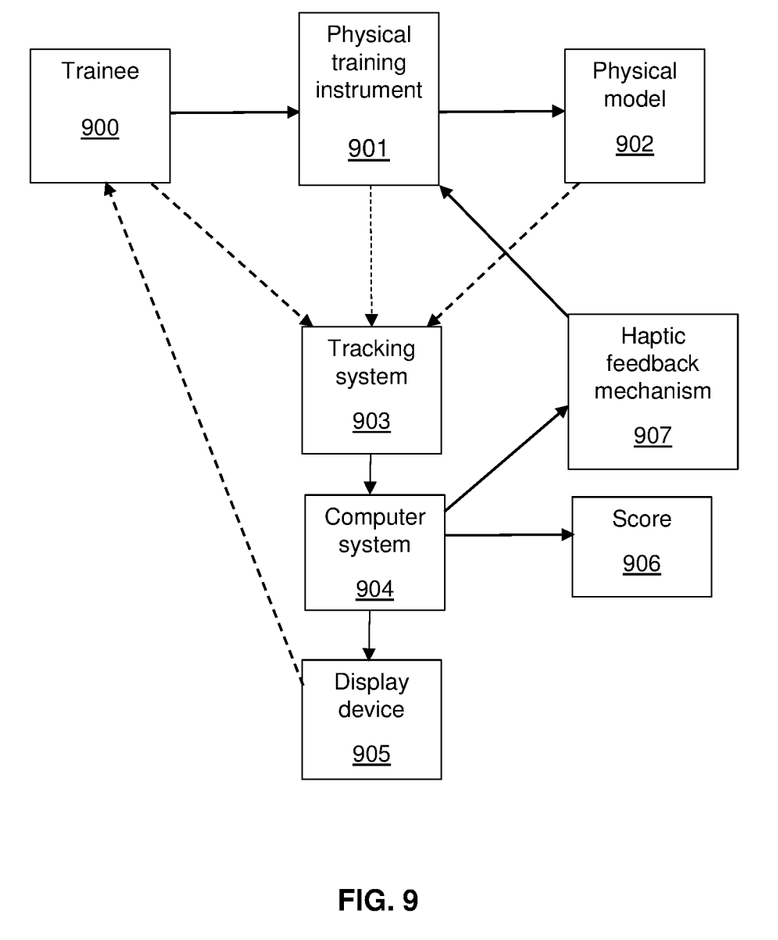
FIG. 9 is a schematic diagram showing the key elements of one preferred embodiment of the invention.

FIG. 9 depicts a preferred embodiment of the surgical training system. In FIG. 9, the dashed lines indicate the transmission and reception of light reflected from the trainee 900, the physical training instrument 901 and the physical model 902, as well has light generated by the display device 905 that is viewable by the trainee 900. The solid lines indicate physical or electronic interaction.

The system is adapted to assist in training and assessing the performance of a trainee 900, such as a medical doctor, resident, student, researcher, equipment technician, or other practitioner, professionals, or personnel, in a surgical procedure on an anatomical region of a body. For example, the surgical procedure may involve performing a craniotomy and resectioning of a brain tumor in the brain of a human patient.

A physical model 902 of the patient's head and brain is employed in the case of a craniotomy and tumor resectioning. The model may include a physical feature representing a brain tumor inside the brain 230 of a training model 902, or the brain tumor to be resectioned may be partly or completely generated (simulated) by the computer system. The trainee manipulates one or more physical training instruments 901 to perform the surgical procedure. The physical training instrument 901 may be a complete surgical instrument suitable for use in actual surgery, or it may be a partial instrument, for example not including a complete cutting tip.

The tracking system 903 tracks the position and orientation of the physical training instrument 901 relative to the physical model 902 as the trainee manipulates the physical training instrument 901 to perform the surgical procedure. In some embodiments, such as where the display device is a head-mounted display, the tracking system 903 also tracks the location of the trainee 900, or more specifically the location of the trainee's head and eyes relative to the physical model 902, and more specifically relative to the portion of the physical model used to generate the augmented physical model upon which the surgical procedure is being performed. The tracking system 903 provides the position and orientation of the physical training instrument 901 to the computer system 904 in real-time as the (simulated) surgical procedure is performed. Updated information may be provided by the tracking system 903 at regular intervals, for example, or may be provided when the tracking system 903 has detected a change in the location or orientation of a physical training instrument 901. Such changes may result from actions by the trainee such as repositioning the physical training instrument 901, which may involve using the physical training instrument 901 to cut and/or remove a portion of the physical model 902 or of the augmented physical model.

In addition to providing the above-described positional information, the tracking system 903 may provide images showing the physical model as the procedure progresses. For example, the tracking system 903 may include a video camera that provides a real-time stream of video showing the portion of the physical model 902 upon which the surgical procedure is being performed to the computer system 904. The physical model 902 will change, for example, as a trainee uses a surgical instrument to physically remove portions of the physical model 902, such as physical tumors disposed therein.

The computer system 904 receives the tracking system information and, based on that information, generates and displays on the display device 905 a display showing an augmented physical model and a depiction of the physical training instrument 901, which may be an augmented physical training instrument, as discussed below. The trainee 900 views the display on the display device 905 and manipulates the physical training instrument 901 while viewing the display in order to perform the surgical procedure. The display device 905 may be a monitor at some distance from the trainee 900, such as 1-5 meters, or it may be a head-mounted display that moves as the trainee's head moves during the procedure.

The augmented physical model 902 is generated by the computer system 905 based on images of the physical model 902 upon which the surgical procedure is being performed with virtual elements rendered by the computer system and superimposed on a digital rendering of the physical model 902 derived from the video images received from the tracking system 903. The extent and nature of the virtual elements varies substantially between different embodiments. In some embodiments, for example, the physical model 902 may include a simulated tumor and neural tracts, whereas in other embodiments some or all of the tumor and neural tracts may be generated by the computer system 904 as virtual elements that are superimposed on a rendering of the physical model 902 by the computer system 904. In some embodiments, the virtual elements include arteries and if an artery is cut or damaged, then the virtual elements may include blood exiting the cut or damaged artery.

The number and extent of virtual features added to the augmented physical model vary significantly between embodiments. In general, ignoring cost, it is preferable to include more elements in the physical model, such as such as neural tracts, blood vessels (including blood), CSF, sub-anatomical structures (e.g. hippocampi, amygdala, etc.), and ventricles. Physical elements that are part of the physical model provide realistic haptic feedback to the trainee whereas this is more difficult to achieve in relation to virtual elements. This is not a significant issue for some elements, such as blood generated as a virtual element, but may be important for some elements such as a tumor being resectioned.

In some embodiments, the virtual elements may include visual highlighting of certain portions of the model to provide information to the trainee 900. This may be done for example to indicate particularly sensitive or important areas for purposes of training the trainee.

Preferably, the display is regenerated and displayed in real-time as the trainee manipulates the physical training instrument 901 and modifies the physical model 902 or the augmented physical model by modifying virtual elements by manipulating the physical training instrument 901. This may be done by continuously augmenting a received video stream of the physical model as it is received and adding virtual elements. The added virtual elements generally change in accordance with the trainee's manipulation of the physical training instrument 901 as the physical model 902 is modified, for example thereby exposing different internal structures that require additional virtual elements. They also change in accordance with the simulated impact of the physical training instrument 901 on the displayed virtual elements.

In all embodiments, the computer system 904 calculates a score 906 based on the performance of the trainee 900 after the trainee 900 has completed the surgical procedure. The score may be, for example a number between 0 and 100 where 0 indicates very poor performance and 100 indicts excellent performance. Alternatively, the score 906 may be multi-dimensional, including multiple component scores, each component score estimating a different aspect of the trainee's performance. The score 906 is based on at least a measure of the accuracy of the surgical procedure performed by the trainee 900. For example, in the case of a tumor resectioning, a simple example of a score 906 is the percentage of the tumor that was removed by the procedure, or, more precisely, the amount of an actual tumor in a patient corresponding to the tumor in the augmented physical model that would have been removed by a surgical instrument corresponding to the physical training instrument 901 by movements of the surgical instrument corresponding to trainee's manipulation of the physical training instrument 901. This may be computed by dividing the amount of the tumor removed by the initial total amount of the tumor, where "amount" may refer to volume, mass or a combination thereof. Equivalently, the score may be based on the amount or percentage of the tumor that was left behind, i.e. not removed by the surgical procedure.

Preferably, the score is a function of multiple measures including the duration of the surgical procedure. Generally, longer durations are undesirable and so the score will be lower the longer the procedure takes.

An example of a surgical procedure to be performed by a trainee 900 is a brain tumor resectioning, which requires the trainee 900 to first perform a craniotomy to gain access to the brain and the tumor. The score may also be based on a measure of the damage to healthy brain tissue caused by the surgical procedure. For example, in the case of a tumor resectioning, one such measure is the distance from the craniotomy to the tumor, which relates to the amount of healthy brain tissue that is likely to have been damaged in order to gain access to the tumor. The longer the path to the target tumor, the more healthy brain cells that are likely to have been damaged. Another example is the amount (or percentage) of non-tumor tissue in the brain that would have been removed or damaged by a surgical instrument corresponding to the physical training instrument by movements of the surgical instrument corresponding to trainee's manipulation of the physical training instrument during the procedure.

Another example of a measure upon which the score may be based is an estimate of the impact of the surgical procedure on neural tracts in the brain. Where an obturator is employed in brain surgery, impact on neural tracts can be measured in terms of the deflection distance of the fiber by the obturator and the angle of impact. Assuming the risk of damage is zero for parallel tracts (no shear damage is observed) and is a maximum for perpendicular tracts, the cosine of the impact angle is a preferred metric to use. A measure can then be calculated as the sum over the number of tracts impacted by the procedure of a track-specific constant multiplied by the deflection distance and multiplied by the cosine of the angle of impact or the square of the cosine of the angle of impact. Where the angle of impact is 0 degrees for perpendicular tracts and 90 degrees for parallel tracts. The track-specific constant is a predetermined value based on the importance of the particular tract. The number generated is a measure that is directly related to the impact of the trajectory, and can be used as a direct comparison to measure tract impact for different targets regardless of depth.

The score may also be based on measures such as an estimate of the negative impact on blood vessels due to the procedure and, in the case of the brain, damage to eloquent areas of the brain which are particularly sensitive. For example, in any measure of damage, the measure may be calculated by weighting estimates of damage to each damaged portion by a constant representing an estimate of the importance of the location of the damaged portion. Similarly, the score may be based on the amount or percentage of blood vessels in the region of the tumor that are left intact and undamaged. The size of the craniotomy may also be factored into the score, with smaller areas being preferred relative to larger areas.

Multiple such measures may be calculated and used to compute an overall score. In some embodiments, the final score may be calculated using a variation of Fitt's law. The approach to calculate individual measures and an overall score may be based on analysis of the performance of an expert performing the surgical procedure. Preferably, the score is derived from analysis of the performance of multiple experts performing the surgical procedure using machine learning techniques.

In some embodiments, the physical training instrument 901 may not be a complete surgical instrument but rather may resemble a portion of a surgical instrument and not include all portions of the surgical instrument. For example, a cutting tip may not be present in the physical training instrument 901. In such embodiments, portions of the surgical instrument not present in the physical training instrument 901 may be generated as a virtual element or elements rendered by the computer system 904 as part of an augmented physical training instrument in the generated display. For example, a virtual cutting tip on an instrument in the generated display may be manipulated by the trainee 900 by manipulating the physical training instrument 901 to resection a tumor generated as a virtual element of the augmented physical model. In such embodiments, since there is little or no physical contact between the physical training instrument 901 and the physical model 902, the system may include a haptic feedback mechanism 907 coupled to the physical training instrument 901 and configured to provide haptic feedback to the trainee 900 under control of the computer system 904 by applying force to the physical training instrument 901 as the trainee 900 moves the physical training instrument 901. The magnitude and direction of the force is calculated by the computer system 905 to approximate what would be experienced by a corresponding surgical instrument in a real operation where the surgical instrument is interacting with the patient's body in a manner corresponding to the interaction of the physical training instrument, in the case of a complete physical training instrument, or otherwise an augmented physical training instrument, with the augmented physical model. In the case of an augmented physical training instrument where the cutting tip is virtual, then most of the haptic feedback would need to be provided by the haptic feedback mechanism 907. In a situation where a full physical training instrument is used to perform a procedure involving primarily physical elements of the augmented physical model, then the haptic feedback mechanism 907 is generally not required as the appropriate forces are created by the interaction of the physical training instrument 901 with the physical model 902.

It will be understood by skilled persons that, while the present invention is primarily intended to train surgeons operating on anatomical regions of a human body, such as a human head and brain, the invention can be used to train surgeons for operating on other living beings, such as mammals.

Generally, a computer, computer system, computing device, client or server, as will be well understood by a person skilled in the art, includes one or more than one electronic computer processor, and may include separate memory, and one or more input and/or output (I/O) devices (or peripherals) that are in electronic communication with the one or more processor(s). The electronic communication may be facilitated by, for example, one or more busses, or other wired or wireless connections. In the case of multiple processors, the processors may be tightly coupled, e.g. by high-speed busses, or loosely coupled, e.g. by being connected by a wide-area network.

A computer processor, or just "processor", is a hardware device for performing digital computations. It is the express intent of the inventors that a "processor" does not include a human; rather it is limited to be an electronic device, or devices, that perform digital computations. A programmable processor is adapted to execute software, which is typically stored in a computer-readable memory. Processors are generally semiconductor based microprocessors, in the form of microchips or chip sets. Processors may alternatively be completely implemented in hardware, with hard-wired functionality, or in a hybrid device, such as field-programmable gate arrays or programmable logic arrays. Processors may be general-purpose or special-purpose off-the-shelf commercial products, or customized application-specific integrated circuits (ASICs). Unless otherwise stated, or required in the context, any reference to software running on a programmable processor shall be understood to include purpose-built hardware that implements all the stated software functions completely in hardware.

Multiple computers (also referred to as computer systems, computing devices, clients and servers) may be networked via a computer network, which may also be referred to as an electronic network or an electronic communications network. When they are relatively close together the network may be a local area network (LAN), for example, using Ethernet. When they are remotely located, the network may be a wide area network (WAN), such as the internet, that computers may connect to via a modem, or they may connect to through a LAN that they are directly connected to.

Computer-readable memory, which may also be referred to as a computer-readable medium or a computer-readable storage medium, which terms have identical (equivalent) meanings herein, can include any one or a combination of non-transitory, tangible memory elements, such as random access memory (RAM), which may be DRAM, SRAM, SDRAM, etc., and nonvolatile memory elements, such as a ROM, PROM, FPROM, OTP NVM, EPROM, EEPROM, hard disk drive, solid state disk, magnetic tape, CDROM, DVD, etc.) Memory may employ electronic, magnetic, optical, and/or other technologies, but excludes transitory propagating signals so that all references to computer-readable memory exclude transitory propagating signals. Memory may be distributed such that at least two components are remote from one another, but are still all accessible by one or more processors. A nonvolatile computer-readable memory refers to a computer-readable memory (and equivalent terms) that can retain information stored in the memory when it is not powered. A computer-readable memory is a physical, tangible object that is a composition of matter. The storage of data, which may be computer instructions, or software, in a computer-readable memory physically transforms that computer-readable memory by physically modifying it to store the data or software that can later be read and used to cause a processor to perform the functions specified by the software or to otherwise make the data available for use by the processor. In the case of software, the executable instructions are thereby tangibly embodied on the computer-readable memory. It is the express intent of the inventor that in any claim to a computer-readable memory, the computer-readable memory, being a physical object that has been transformed to record the elements recited as being stored thereon, is an essential element of the claim.

Software may include one or more separate computer programs configured to provide a sequence, or a plurality of sequences, of instructions to one or more processors to cause the processors to perform computations, control other devices, receive input, send output, etc.

It is intended that the invention includes computer-readable memory containing any or all of the software described herein. In particular, the invention includes such software stored on non-volatile computer-readable memory that may be used to distribute or sell embodiments of the invention or parts thereof.

Where, in this document, a list of one or more items is prefaced by the expression "such as" or "including", is followed by the abbreviation "etc.", or is prefaced or followed by the expression "for example", or "e.g.", this is done to expressly convey and emphasize that the list is not exhaustive, irrespective of the length of the list. The absence of such an expression, or another similar expression, is in no way intended to imply that a list is exhaustive. Unless otherwise expressly stated or clearly implied, such lists shall be read to include all comparable or equivalent variations of the listed item(s), and alternatives to the item(s), in the list that a skilled person would understand would be suitable for the purpose that the one or more items are listed.

The specific embodiments described above have been shown by way of example, and it should be understood that these embodiments may be susceptible to various modifications and alternative forms. It should be further understood that the claims are not intended to be limited to the particular forms disclosed, but rather to cover modifications, equivalents, and alternatives falling within the spirit and scope of this disclosure.

We claim:

1. A mixed reality surgical training system for training performance of a surgical procedure on an anatomical region of a body, the system comprising:
   a physical model of the anatomical region;
   a physical training instrument;
   a tracking system configured to track a location and an orientation of the physical training instrument relative to the physical model;
   a display device viewable by a trainee; and
   a computer system electronically coupled with the tracking system and the display device, the computer system being configured to:
      receive from the tracking system information indicating the location and orientation of the physical training instrument;
      in real time, generate and display, on the display device, a representation of an augmented physical model and the physical training instrument, the display updated based on changes in the location and orientation of the physical training instrument relative to the physical model as the physical training instrument is manipulated to perform the surgical procedure by continuously augmenting a received video stream of the physical model as the video stream is received and adding virtual elements; and
      after the surgical procedure is completed, calculate a score based on the performance of the surgical procedure and store the score in a computer readable memory, the score based on a measure of accuracy of the performance of the surgical procedure,
   the anatomical region comprising a portion of a mammalian brain having a tumor, the augmented physical model comprising a simulated tumor, the surgical procedure comprising at least one of: a craniotomy, a resection of the tumor, and removal of an intracranial hemorrhage, and the score comprising a measure of the damage to healthy brain tissue caused by the surgical procedure, and
   the physical model configured to approximate at least one of a size and shape of an anatomical region of a patient on which the surgical procedure is to be performed, and whereby training performance of the surgical procedure is provided.

2. The surgical training system of claim 1, wherein the tracking system comprises at least one of an infrared camera and a video camera that provides a real-time stream of video showing a portion of the physical model upon which the surgical procedure is being performed, and wherein the computer system generates and updates the augmented physical model based on the video.

3. The surgical training system of claim 1, wherein the generated display comprises the virtual elements rendered by the computer system and superimposed on a digital rendering of the physical model.

4. The surgical training system of claim 3, wherein the virtual elements comprise highlighting of a portion of the digital rendering of the physical model.

5. The surgical training system of claim 3, wherein the anatomical region comprises a portion of a mammalian head, the virtual elements comprise neural tracts in a brain and the score is based on a tract impact score that provides a measure of the impact of the surgical procedure on the neural tracts.

6. The surgical training system of claim 1, wherein the score is further based on the duration of the surgical procedure.

7. The surgical training system of claim 1, wherein the score is calculated based on the distance from the craniotomy to the tumor.

8. The surgical training system of claim 1, wherein the score is calculated based on the amount of non-tumor tissue in the brain that would have been removed or damaged by a surgical instrument corresponding to the physical training instrument by movements of the surgical instrument corresponding to trainee's manipulation of the physical training instrument.

9. The surgical training system of claim 1, wherein the score is calculated based on an estimate of the impact of the surgical procedure on neural tracts in the brain.

10. The surgical training system of claim 1, wherein the score is calculated based on the amount of the tumor that would have been removed by a surgical instrument corresponding to the physical training instrument by movements of the surgical instrument corresponding to manipulation of the physical training instrument.

11. The surgical training system of claim 1, wherein the computer system further generates and displays as part of the augmented physical model an artery proximate to the tumor.

12. The surgical training system of claim 1, wherein the score is calculated using a method derived from analysis of a performance of an expert performing the surgical procedure.

13. The surgical training system of claim 12, wherein the score is calculated using a method derived from analysis of a performance of a plurality of experts performing the surgical procedure using machine learning.

14. The surgical training system of claim 1, wherein the display device comprises a head-mounted display configured for wear by the trainee.

15. The surgical training system of claim 14, wherein the tracking system is further configured to track a location of the trainee's head relative to the physical model, wherein the display is generated from the perspective of the trainee based on the location of the trainee's head, and wherein the display is updated as the location of the trainee's head changes.

16. The surgical training system of claim 15, further comprising a head-mounted display worn by a trainer, wherein the tracking system is further configured to track the location of the trainer's head relative to the physical model, wherein the computer system is further configured to generate and display on the head-mounted display worn by the trainer a display comprising the augmented physical model and the physical training instrument from the perspective of the trainer, wherein the display on the head-mounted display worn by the trainer is updated based on changes in the location and orientation of the physical training instrument relative to the physical model as the trainee manipulates the physical training instrument to perform the surgical procedure, and wherein the display on the head-mounted display worn by the trainer is updated as the location of the trainer's head changes.

17. The surgical training system of claim 1, wherein the computer system is further configured to generate and display on the display device an augmented physical training instrument, wherein the location and orientation of the augmented physical training instrument relative to the augmented physical model as depicted in the image are based on the location and orientation of the physical training instrument relative to the physical model, and wherein the displayed augmented physical training instrument is updated on the display device by the computer system as the trainee manipulates the physical training instrument.

18. The surgical training system of claim 17, wherein the physical training instrument resembles a portion of a surgical instrument, and wherein the augmented physical training instrument comprises a digital rendering of the physical training instrument augmented by a tip portion generated by the computer system so that the augmented physical training instrument appears on the display device to be the surgical instrument.

19. The surgical training system of claim 17, wherein, as the trainee manipulates the physical training instrument, the computer system repeatedly generates and displays on the display device the augmented physical model depicting simulated effects of the surgical instrument on the anatomical region.

20. The surgical training system of claim 17, further including a haptic feedback mechanism coupled with the physical training instrument and configured to provide haptic feedback to the trainee under control of the computer system by applying force to the physical training instrument as the trainee moves the physical training instrument, the force, calculated by the computer system, comprising a magnitude and a direction experienced by a corresponding surgical instrument interacting with the patient in an actual surgical procedure in a manner corresponding to that of the physical training instrument.

* * * * *